United States Patent
Chowaniec

(10) Patent No.: US 10,952,726 B2
(45) Date of Patent: Mar. 23, 2021

(54) HANDHELD ELECTROMECHANICAL SURGICAL INSTRUMENTS

(71) Applicant: Covidien LP, Mansfield, MA (US)

(72) Inventor: Matthew Chowaniec, Madison, CT (US)

(73) Assignee: Covidien LP, Mansfield, MA (US)

( * ) Notice: Subject to any disclaimer, the term of this patent is extended or adjusted under 35 U.S.C. 154(b) by 373 days.

(21) Appl. No.: 15/355,823

(22) Filed: Nov. 18, 2016

(65) Prior Publication Data

US 2017/0164945 A1  Jun. 15, 2017

Related U.S. Application Data

(60) Provisional application No. 62/265,631, filed on Dec. 10, 2015.

(51) Int. Cl.
*A61B 17/072* (2006.01)
*A61B 17/29* (2006.01)
(Continued)

(52) U.S. Cl.
CPC ............. *A61B 17/07207* (2013.01); *A61B 2017/0046* (2013.01); *A61B 2017/00367* (2013.01);
(Continued)

(58) Field of Classification Search
CPC .......... A61B 2017/00367; A61B 2017/00398; A61B 2017/0046; A61B 2017/2925;
(Continued)

(56) References Cited

U.S. PATENT DOCUMENTS 3,227,154 A   1/1966 Cook
5,230,704 A   7/1993 Moberg et al.
(Continued)

FOREIGN PATENT DOCUMENTS

CN  102028509 A  4/2011
CN  103211635 A  7/2013
(Continued)

OTHER PUBLICATIONS

Chinese Office Action (with English translation) dated Dec. 25, 2015, corresponding to Chinese Application No. 201310012945.0; 16 total pages.
(Continued)

*Primary Examiner* — Anna K Kinsaul
*Assistant Examiner* — Daniel Jeremy Leeds

(57) ABSTRACT

A surgical instrument includes a power pack, an outer shell housing configured to selectively encase the power pack, and an adapter assembly configured to selectively couple the outer shell housing to a loading unit. The outer shell housing includes a motor and a drive shaft coupled to and rotatable by the motor. The outer shell housing includes a drive member supported in a distal portion thereof. The drive member is configured to selectively couple to the drive shaft. The adapter assembly has a drive member supported in its proximal end. The drive member of the adapter assembly is configured to selectively couple to the drive member of the outer shell housing such that rotation of the drive shaft actuates movement of the drive member of the adapter assembly via the drive member of the outer shell housing.

7 Claims, 10 Drawing Sheets

(51) Int. Cl.
 *A61B 17/00* (2006.01)
 *A61B 90/00* (2016.01)
(52) U.S. Cl.
 CPC ............ *A61B 2017/00398* (2013.01); *A61B 2017/00473* (2013.01); *A61B 2017/00477* (2013.01); *A61B 2017/00734* (2013.01); *A61B 2017/07271* (2013.01); *A61B 2017/07285* (2013.01); *A61B 2017/2925* (2013.01); *A61B 2090/0813* (2016.02)
(58) Field of Classification Search
 CPC .......... A61B 2017/00477; A61B 34/35; A61B 34/71; A61B 17/115
 USPC .................................................... 227/181.1
 See application file for complete search history.

(56) References Cited

U.S. PATENT DOCUMENTS

| | | | |
|---|---|---|---|
| 5,401,241 A | 3/1995 | Delany | |
| 5,499,992 A | 3/1996 | Meade et al. | |
| 5,746,759 A | 5/1998 | Meade et al. | |
| 5,752,972 A | 5/1998 | Hoogeboom | |
| 5,928,255 A | 7/1999 | Meade et al. | |
| 5,931,849 A | 8/1999 | Desvignes et al. | |
| 6,206,844 B1 | 3/2001 | Reichel et al. | |
| 7,468,041 B2 | 12/2008 | Rhodes et al. | |
| 8,221,449 B2 | 7/2012 | Gadberry et al. | |
| 8,894,647 B2 | 11/2014 | Beardsley et al. | |
| 9,155,529 B2 | 10/2015 | Beardsley et al. | |
| 2002/0099259 A1* | 7/2002 | Anderson | A61B 17/0401 600/29 |
| 2004/0015051 A1* | 1/2004 | Sudakov | A61B 1/31 600/105 |
| 2004/0116952 A1 | 6/2004 | Sakurai et al. | |
| 2006/0041265 A1* | 2/2006 | Shackelford, Sr. | A61B 17/3211 606/167 |
| 2006/0226195 A1 | 10/2006 | Scirica et al. | |
| 2008/0167671 A1* | 7/2008 | Giordano | A61B 17/07207 606/167 |
| 2009/0143805 A1* | 6/2009 | Palmer | A61B 17/320092 606/169 |
| 2010/0057106 A1 | 3/2010 | Sorrentino et al. | |
| 2010/0137895 A1* | 6/2010 | Smith | A61B 17/32093 606/185 |
| 2010/0320252 A1* | 12/2010 | Viola | A61B 17/07207 227/176.1 |
| 2011/0009694 A1* | 1/2011 | Schultz | A61B 1/00052 600/109 |
| 2011/0017801 A1 | 1/2011 | Zemlok et al. | |
| 2011/0125138 A1* | 5/2011 | Malinouskas | A61B 17/068 606/1 |
| 2011/0306952 A1 | 12/2011 | Chen et al. | |
| 2012/0089131 A1* | 4/2012 | Zemlok | A61B 17/07207 606/1 |
| 2012/0116266 A1 | 5/2012 | Houser et al. | |
| 2012/0238829 A1 | 9/2012 | Shelton, IV et al. | |
| 2012/0239010 A1 | 9/2012 | Shelton, IV et al. | |
| 2012/0253116 A1 | 10/2012 | Sniffin et al. | |
| 2012/0253328 A1 | 10/2012 | Cunningham et al. | |
| 2013/0072952 A1 | 3/2013 | Storz | |
| 2013/0165774 A1 | 6/2013 | Nocca | |
| 2013/0184704 A1* | 7/2013 | Beardsley | A61B 18/14 606/41 |
| 2013/0184730 A1* | 7/2013 | Beardsley | A61B 17/07207 606/174 |
| 2013/0319706 A1* | 12/2013 | Nicholas | B25F 3/00 173/29 |
| 2013/0334281 A1* | 12/2013 | Williams | A61B 17/068 227/176.1 |
| 2014/0025046 A1* | 1/2014 | Williams | A61B 17/07207 606/1 |
| 2014/0246471 A1* | 9/2014 | Jaworek | A61B 17/068 227/175.1 |
| 2014/0246477 A1* | 9/2014 | Koch, Jr. | A61B 17/068 227/180.1 |
| 2014/0276761 A1* | 9/2014 | Parihar | A61B 18/12 606/34 |
| 2014/0352463 A1* | 12/2014 | Parihar | F16H 19/02 74/25 |
| 2015/0014392 A1* | 1/2015 | Williams | A61B 17/07207 227/180.1 |
| 2015/0157354 A1* | 6/2015 | Bales, Jr. | B06B 1/0223 606/169 |
| 2015/0342601 A1 | 12/2015 | Williams et al. | |
| 2015/0366560 A1* | 12/2015 | Chen | A61B 17/00 227/176.1 |
| 2016/0008080 A1 | 1/2016 | Beardsley et al. | |
| 2016/0089175 A1* | 3/2016 | Hibner | A61B 17/285 606/206 |
| 2016/0095585 A1* | 4/2016 | Zergiebel | A61B 34/74 606/1 |
| 2016/0106401 A1* | 4/2016 | Beardsley | A61B 17/00 606/1 |
| 2016/0118201 A1* | 4/2016 | Nicholas | H01H 9/26 200/43.17 |
| 2016/0235476 A1* | 8/2016 | Wand | A61B 18/14 |
| 2016/0249918 A1* | 9/2016 | Shelton, IV | H02J 7/0013 227/175.1 |
| 2016/0249919 A1* | 9/2016 | Savage | A61B 17/072 227/175.1 |
| 2016/0249945 A1* | 9/2016 | Shelton, IV | A61B 17/068 606/171 |
| 2016/0324518 A1* | 11/2016 | Nicholas | A61B 17/072 |
| 2017/0281171 A1* | 10/2017 | Shelton, IV | A61B 17/3211 |

FOREIGN PATENT DOCUMENTS

| | | |
|---|---|---|
| CN | 103230285 A | 8/2013 |
| CN | 104688289 A | 6/2015 |
| EP | 0804124 B1 | 7/1999 |
| EP | 2668910 A2 | 12/2013 |
| EP | 2875842 A1 | 5/2015 |
| EP | 2881046 A2 | 6/2015 |
| EP | 2932910 A2 | 10/2015 |
| JP | H09538 A | 1/1997 |
| JP | 2000254141 A | 9/2000 |
| JP | 2010051805 A | 3/2010 |
| JP | 2011078772 A | 4/2011 |
| JP | 2013515566 A | 5/2013 |
| JP | 2013128768 A | 7/2013 |
| JP | 2013144108 A | 7/2013 |
| JP | 2014528758 A | 10/2014 |
| JP | 2015205170 A | 11/2015 |
| WO | 2009097585 A1 | 8/2009 |

OTHER PUBLICATIONS

European Search Report, dated Mar. 13, 2015, corresponding to European Application No. 13 15 1037.2; 7 pages.
Chinese First Office Action (with English translation), dated Jan. 26, 2016, corresponding to Chinese Application No. 201310013044.3; 16 total pages.
Chinese Second Office Action (with English translation), dated Aug. 4, 2016, corresponding to Chinese Application No. 201310012945.0; 18 total pages.
Japanese Office Action (with English translation), dated Aug. 30, 2016, corresponding to Japanese Application No. 2013-000854; 8 total pages.
Australian Patent Examination Report No. 1, dated Sep. 20, 2016, corresponding to Australian Application No. 2013200112; 3 pages.
Australian Patent Examination Report 1, dated Sep. 5, 2016, corresponding to Australian Application No. 2013200115; 3 pages.
European Communication dated Mar. 5, 2018, correspondiing to counterpart European Application No. 16 203198-3; 5 pages.
European Search Report dated Mar. 28, 2017, corresponding to European Application No. 16203198.3; 6 pages.

(56) References Cited

OTHER PUBLICATIONS

European Search Report dated Mar. 24, 2017, corresponding to European Application No. 16199748.1; 5 pages.
English translation of Chinese Office Action dated Jun. 3, 2020, corresponding to counterpart Chinese Application No. 201611132702.0; 13 pages.
Japanese Office Action dated Nov. 4, 2020, issued in corresponding JP Appln. No. 2016-238597, 5 pages.

* cited by examiner

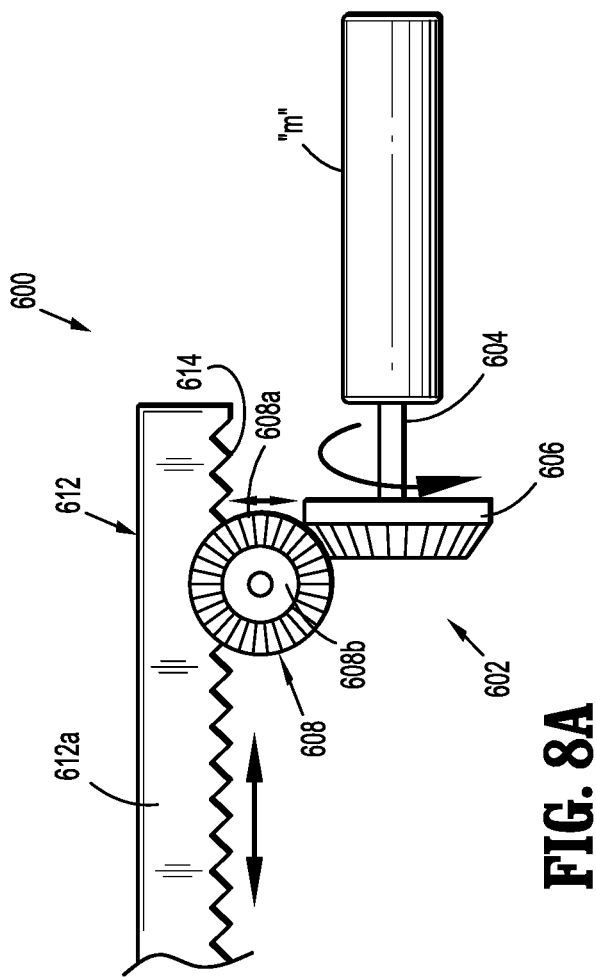
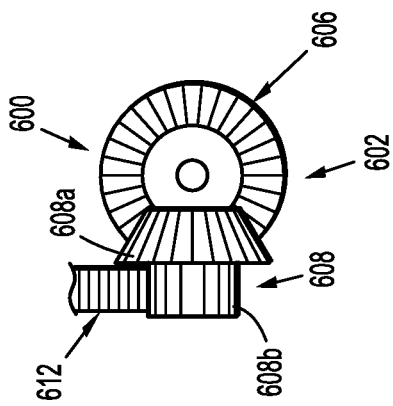
FIG. 8A
FIG. 8B

HANDHELD ELECTROMECHANICAL SURGICAL INSTRUMENTS

CROSS-REFERENCE TO RELATED APPLICATIONS

This application claims the benefit of and priority to U.S. Provisional Patent Application No. 62/265,631, filed Dec. 10, 2015, the entire disclosure of which is incorporated by reference herein.

BACKGROUND

1. Technical Field

The present disclosure relates to surgical instruments. More specifically, the present disclosure relates to handheld electromechanical surgical instruments for performing surgical procedures.

2. Background of Related Art

One type of surgical instrument is a linear clamping, cutting and stapling instrument. Such an instrument may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this instrument, one of the two scissors-styled gripping elements, such as the anvil portion, moves or pivots relative to the overall structure, whereas the other gripping element remains fixed relative to the overall structure. The actuation of this scissoring mechanism (the pivoting of the anvil portion) is controlled by a grip trigger maintained in the handle.

In addition to the gripping elements, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The gripping elements may be integrally formed with the shaft or may be detachable such that various scissoring and stapling elements may be interchangeable.

A number of surgical instrument manufacturers have developed product lines with proprietary powered drive systems for operating and/or manipulating the surgical instrument. In many instances the surgical instruments include a powered handle assembly, which is reusable, and a disposable end effector or the like that is selectively connected to the powered handle assembly prior to use and then disconnected from the end effector following use in order to be disposed of or in some instances sterilized for re-use.

Many of the existing end effectors for use with many of the existing powered handle assemblies are driven by a linear force. For example, end effectors for performing endo-gastrointestinal anastomosis procedures, end-to-end anastomosis procedures and transverse anastomosis procedures, each typically require a linear driving force in order to be operated. As such, these end effectors cannot be directly attached to handle assemblies that use a rotary motion to deliver power or the like.

In order to make the linear driven end effectors compatible with powered surgical handle assemblies that use a rotary motion to deliver power, a need exists for a way to convert rotation originating in the handle assembly into linear motion for driving the operations of the attached end effector. Typically, adapters that intercouple an end effector with a powered handle assembly are used to provide this conversion of rotation to translation.

Accordingly, a need exists for alternative ways of converting the rotational motion originating in the handle assemblies into linear motion.

SUMMARY

In one aspect of the present disclosure, a surgical instrument is provided, which includes a power pack, an outer shell housing, and an adapter assembly. The power pack includes a motor and a drive shaft coupled to and rotatable by the motor. The outer shell housing is configured to selectively encase the power pack therein and includes a first drive member supported in a distal portion of the outer shell housing. The first drive member is configured to selectively couple to the drive shaft. The adapter assembly has a proximal end configured to selectively couple to the outer shell housing, and a distal end configured to couple to a loading unit. The adapter assembly has a second drive member supported in the proximal end. The second drive member is configured to selectively couple to the first drive member such that rotation of the drive shaft actuates the second drive member through the first drive member.

In some embodiments, the outer shell housing may be transitionable between an open configuration and a closed configuration. In the open configuration, the power pack may be insertable and/or removable from the outer shell housing. In the closed configuration, the power pack may be enclosed within the outer shell housing. The outer shell housing may have a proximal portion pivotably coupled to the distal portion of the outer shell housing such that in the open configuration, a portion of the proximal portion of the outer shell housing is spaced from a corresponding portion of the distal portion of the outer shell housing.

In some embodiments, in the closed configuration, the portion of the proximal portion of the outer shell housing may be connected to the corresponding portion of the distal portion of the outer shell housing. In the closed configuration, the drive shaft may be operably connected to the first drive member. In the open configuration, the drive shaft may be disconnected from the first drive member.

In some embodiments, rotation of the drive shaft may axially move the first drive member when the first drive member is operably connected to the drive shaft of the power pack.

In some embodiments, the drive shaft may be a lead screw. The first drive member of the outer shell housing may be an elongated nut threadingly engaged to the lead screw such that rotation of the lead screw axially moves the elongated nut relative to the lead screw. The first drive member may include a nut threadingly engaged to the lead screw, and a post extending from the nut. The post may have a mating part configured to detachably mate with a corresponding mating part of the second drive member such that rotation of the lead screw translates the first drive member therealong to translate the second drive member.

In some embodiments, the surgical instrument may further include a coupling gear configured to interconnect the drive shaft and the first drive member. The drive shaft may include a first bevel gear configured to operably engage the coupling gear. The coupling gear may include a second bevel gear in operable engagement with the first bevel gear, and a spur gear extending from the second bevel gear and in operable engagement with the first drive member."

In some embodiments, the first drive member may be a longitudinal rack having teeth in operable engagement with the spur gear of the coupling gear such that rotation of the first bevel gear axially moves the longitudinal rack. The first drive member may include two racks pivotably joined to one another. Each rack may have teeth in operable engagement with the spur gear of the coupling gear such that rotation of the first bevel gear axially moves at least one of the two racks.

In some embodiments, the first drive member may be an elongated ribbon including a proximal end and a distal end. The proximal end of the ribbon is disposed about the spur gear and defines a plurality of slits for receipt of teeth of the spur gear. The distal end of the ribbon is disposed within a linear track defined in the outer shell housing such that rotation of the coupling gear rotates the proximal end of the ribbon to axially move the distal end of the ribbon through the linear track.

In some embodiments, the second drive member may have a proximal end configured for snap fit engagement with a distal end of the drive member of the outer shell housing.

In another aspect of the present disclosure, a handle assembly is provided, which includes a power pack and an outer shell housing. The power pack includes a motor and a drive shaft coupled to and rotatable by the motor. The outer shell housing is configured to selectively encase the power pack therein and includes a drive member supported in a distal portion of the outer shell housing. The drive member is configured to selectively couple to the drive shaft of the power pack and a drive member of an adapter assembly. The drive shaft is configured to actuate movement of the drive member of the outer shell housing upon rotation of the drive shaft.

In yet another aspect of the present disclosure, an outer shell housing for selectively encasing a power pack therein is provided. The outer shell housing includes a proximal portion defining a cavity therein, and a distal portion defining a cavity therein. The distal portion is pivotably coupled to the proximal portion between an open configuration, in which a portion of the proximal portion is spaced from a corresponding portion of the distal portion, and a closed configuration, in which the portion of the proximal portion is connected to the corresponding portion of the distal portion. The outer shell housing further includes a drive member supported in the distal portion. The drive member is configured to selectively interconnect a drive shaft of a power pack and a drive member of an adapter assembly.

In some embodiments, in the closed configuration, the proximal portion and the distal portion may cooperatively define an internal cavity configured for encasing a power pack. In the open configuration, a power pack may be insertable and/or removable from the outer shell housing.

The present disclosure relates to electromechanical surgical instruments for performing surgical procedures.

BRIEF DESCRIPTION OF THE DRAWINGS

Embodiments of the present disclosure are described herein with reference to the accompanying drawings, wherein:

FIG. 8A is a side view of yet another embodiment of a drive assembly that extends longitudinally through the power pack of FIG. 3, the outer shell housing of FIG. 3, and the adapter assembly of FIG. 1;

FIG. 8B is front view of the drive assembly of FIG. 8A;

DETAILED DESCRIPTION OF EMBODIMENTS

Figure 1:
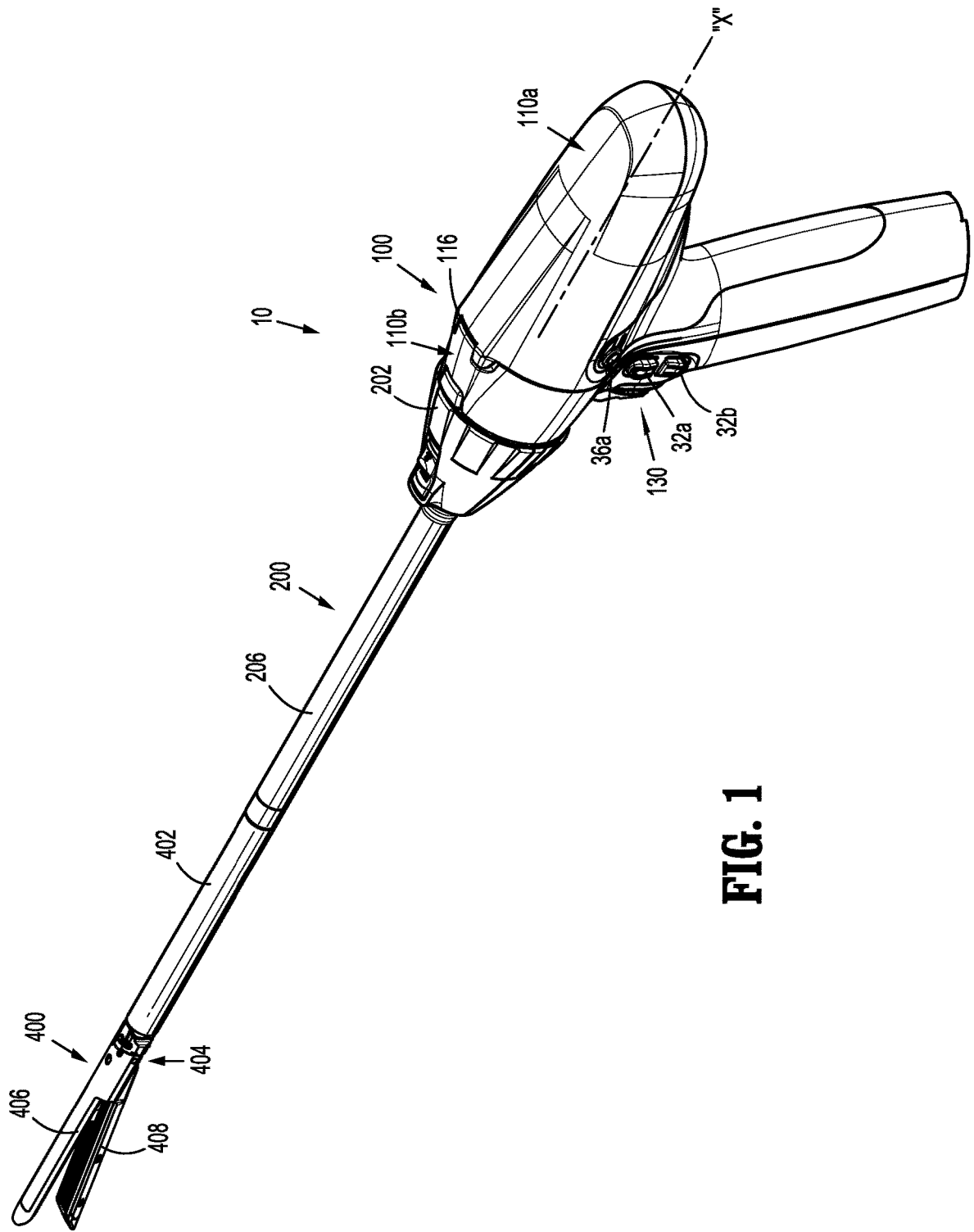
FIG. 1 is a perspective view of a handheld surgical instrument including a handle assembly, an adapter assembly, and a surgical loading unit, in accordance with an embodiment of the present disclosure.
Figure 2:
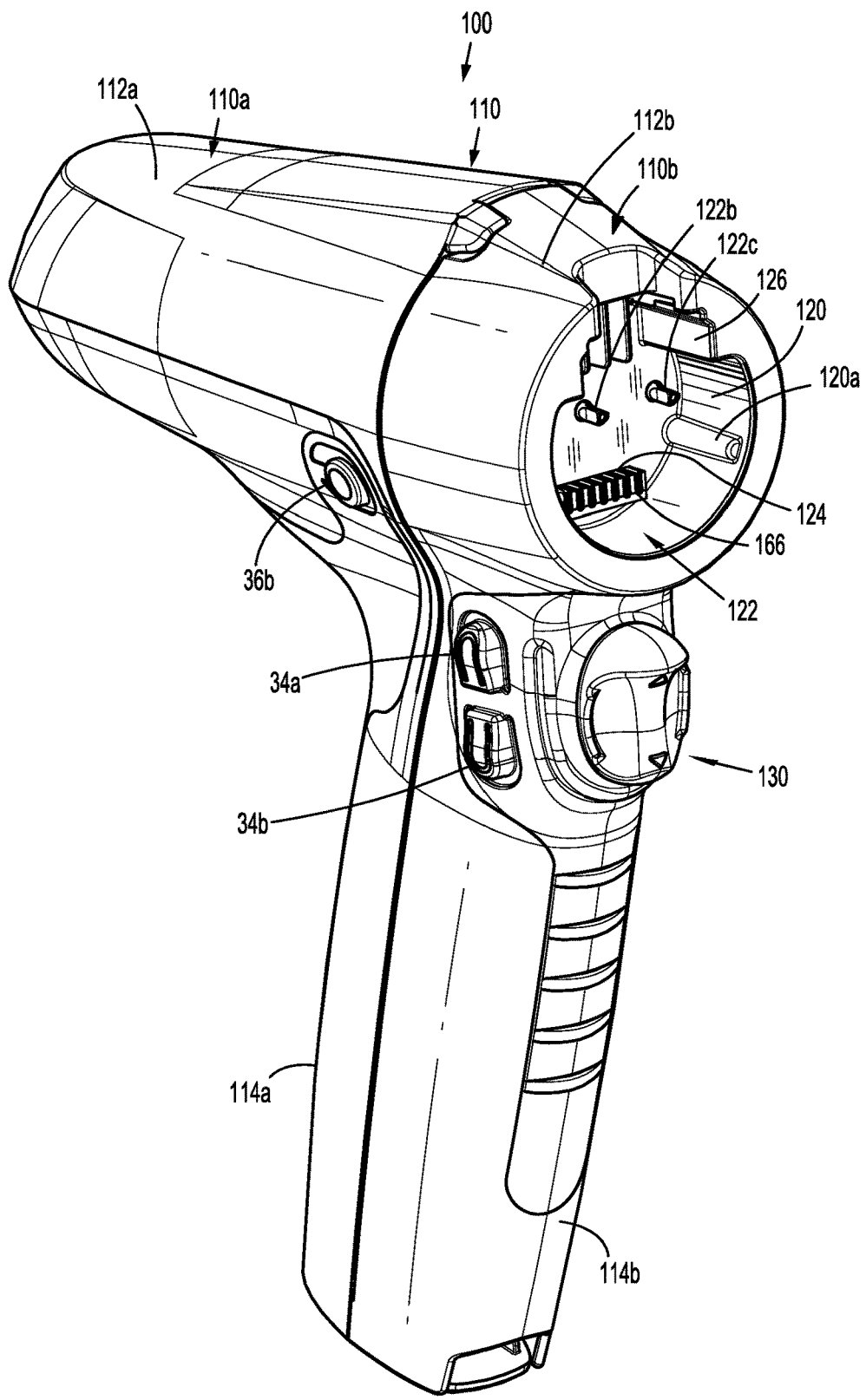
FIG. 2 is a perspective view of the handle assembly of FIG. 1.

Embodiments of the presently disclosed surgical instruments including handle assemblies, adapter assemblies, and drive assemblies, are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

With reference to FIG. 1, a surgical instrument, in accordance with an embodiment of the present disclosure, is generally designated as 10, and is in the form of a powered hand held electromechanical instrument configured for performing various surgical functions, for example, stapling and cutting tissue. Surgical instrument 10 includes a handle assembly 100 configured for selective connection with an adapter assembly 200, and, in turn, adapter assembly 200 is configured for selective connection with end effectors or single use loading units ("SULU's") 400. As described in detail below, surgical instrument 10 may include a variety of drive assemblies, for example, a drive assembly 300 shown in FIG. 5, configured to transfer motion originating from handle assembly 100, through adapter assembly 200, and to SULU 400.

As illustrated in FIGS. 1-4C, handle assembly 100 of surgical instrument 10 includes an outer shell housing 110 and a power pack 101 configured to be selectively received and substantially encased by outer shell housing 110. Outer shell housing 110 includes a proximal portion or proximal half-section 110a and a distal portion or distal half-section 110b. Half-sections 110a, 110b of outer shell housing 110 are pivotably connected to one another by a hinge 116 located along an upper edge of distal half-section 110b and proximal half-section 110a. When joined, proximal and distal half-sections 110a, 110b define a shell cavity 110c therein in which power-pack 101 is selectively situated. Proximal and distal half-sections 110a, 110b are divided along a plane that is perpendicular to a longitudinal axis "X" of adapter assembly 200. Each of proximal and distal half-sections 110a, 110b includes a respective upper shell portion 112a, 112b, and a respective lower shell portion 114a, 114b. Lower shell portions 112a, 112b define a snap closure feature 118 for selectively securing lower shell portions 112a, 112b to one another and for maintaining outer shell housing 110 in a closed condition.

Proximal half-section 110a is sized and shaped to house a majority of power pack 101 therein. Proximal half-section 110a of shell housing 110 supports a right-side control button 36a and a left-side control button 36b. Right-side control button 36a and left-side control button 36b are capable of being actuated upon application of a corresponding force thereto or a depressive force thereto.

Figure 4A:
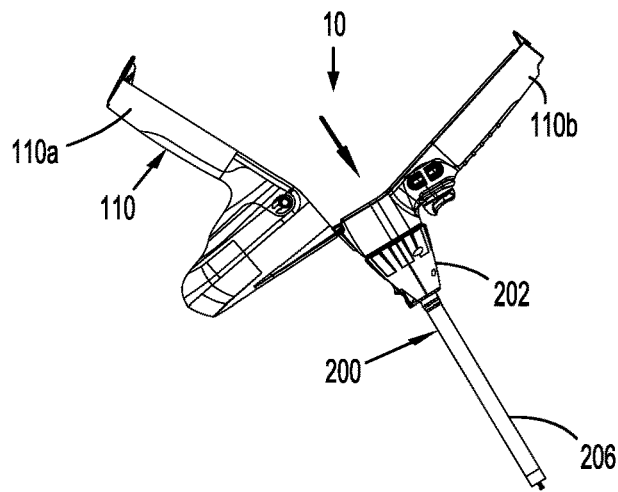
FIG. 4A is a side view of the surgical instrument of FIG. 1 illustrating the outer shell housing of FIG. 3 in an open configuration
Figure 4B:
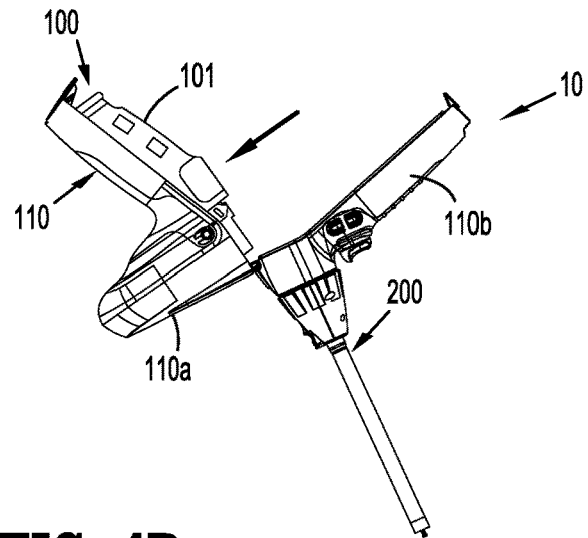
FIG. 4B is a side view of the surgical instrument of FIG. 1 illustrating the outer shell housing of FIG. 3 in the open configuration with the power pack disposed therein.
Figure 4C:
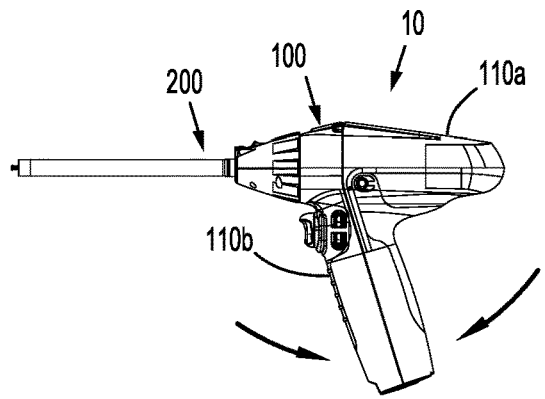
FIG. 4C is a side view of the surgical instrument of FIG. 1 illustrating the outer shell housing of FIG. 3 in a closed configuration.

Distal half-section 110b of outer shell housing 110 covers a distal facing portion of power pack 101 when outer shell housing 110 is in the closed configuration, as shown in FIG. 4C. Distal half-section 110b of outer shell housing 110 non-rotatably supports a drive member 312 of drive assembly 300 therein, as will be described in detail below with reference to FIG. 5. Distal half-section 110b defines a connecting portion 120 configured to accept a corresponding drive coupling assembly (not shown) of adapter assembly 200. Specifically, distal half-section 110b of outer shell housing 110 has a recess 122 that receives a portion (not shown) of the drive coupling assembly (not shown) of adapter assembly 200 when adapter assembly 200 is mated to handle assembly 100. Connecting portion 120 of distal half-section 110b defines a pair of axially extending guide rails 120a, 120b projecting radially inward from inner side surfaces thereof. Guide rails 120a, 120b assist in rotationally orienting adapter assembly 200 relative to handle assembly 100 when adapter assembly 200 is mated to handle assembly 100. Connecting portion 120 of distal half-section 110b defines three apertures 122a, 122b, 122c formed in a distally facing surface thereof and which are arranged in a common plane or line with one another. Connecting portion 120 of distal half-section 110b also defines an elongate slot 124 to contain a connector 166 also formed in the distally facing surface thereof. Connecting portion 120 of distal half-section 110b further defines a female connecting feature 126 formed in a surface thereof. Female connecting feature 126 selectively engages with a male connecting feature (not shown) of adapter assembly 200. It is contemplated that distal half-section 110b may assume a variety of shapes that are each configured for non-rotatably housing a drive member of a drive assembly, for example, drive member 312 of drive assembly 300 shown in FIG. 5.

Distal half-section 110b of outer shell housing 110 supports a distal facing toggle control button 130. Toggle control button 130 is capable of being actuated in a left, right, up and down direction upon application of a corresponding force thereto or a depressive force thereto. Distal half-section 110b of outer shell housing 110 supports a right-side pair of control buttons 32a, 32b; and a left-side pair of control button 34a, 34b. Right-side control buttons 32a, 32b and left-side control buttons 34a, 34b are capable of being actuated upon application of a corresponding force thereto or a depressive force thereto.

Outer shell housing 110 is fabricated from a polycarbonate or similar polymer, and is clear or transparent or may be overmolded. In some embodiments, outer shell housing 110 may be fabricated from any suitable material that can be sterilized, for example, by way of autoclaving.

Figure 3:
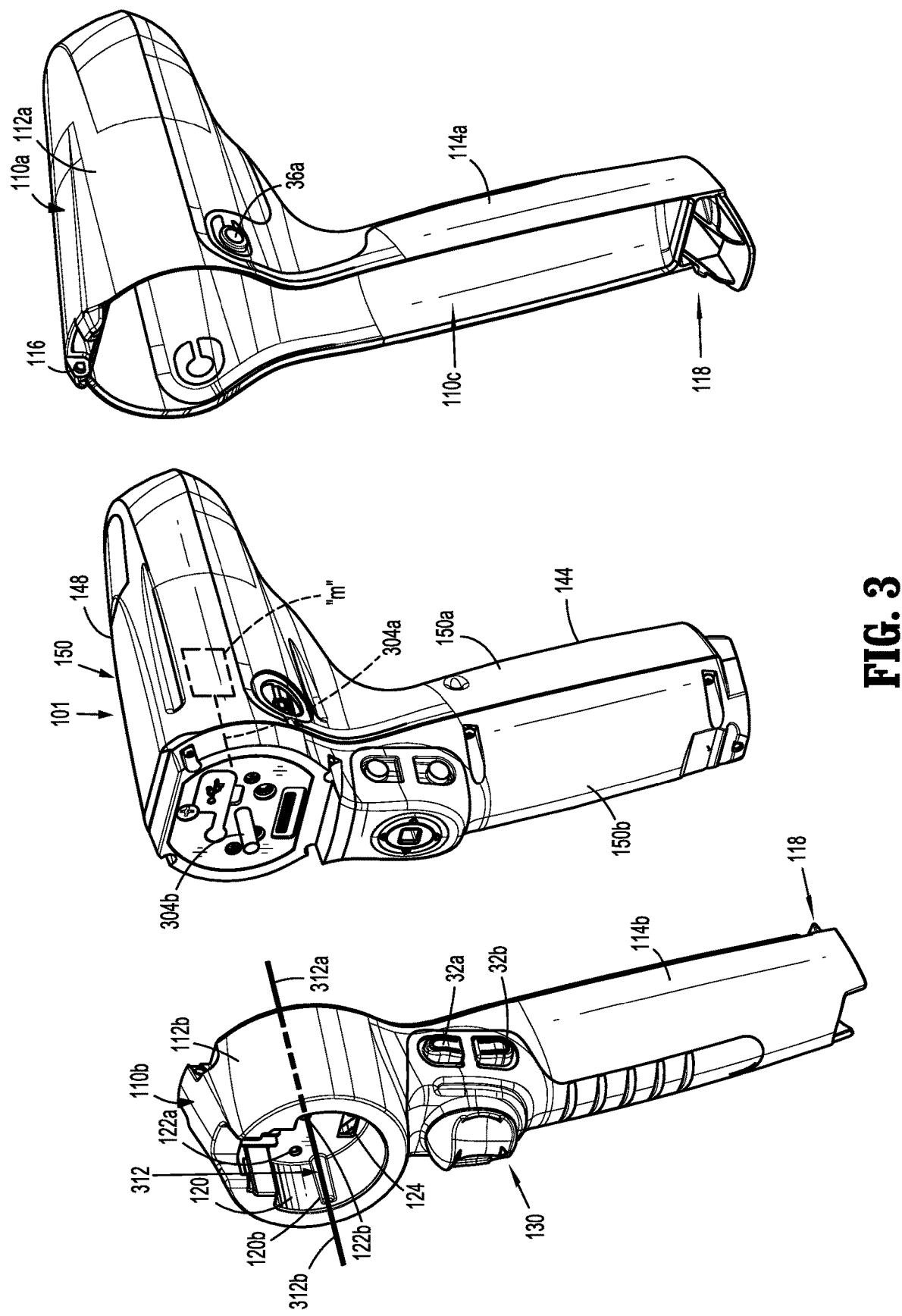
FIG. 3 is a front perspective view, with parts separated, of the handle assembly of FIG. 2 including an outer shell housing and a power pack.

With reference to FIGS. 3-4C, power-pack 101 of handle assembly 100 is configured for receipt within outer shell housing 110 and for powering the functions of surgical instrument 10. Power-pack 101 of handle assembly 100 includes an inner handle housing 150 having a lower housing portion 144 and an upper housing portion 148 extending from and/or supported on lower housing portion 144. Lower housing portion 144 and upper housing portion 148 are separated into a proximal half-section 150a and a distal half-section 150b connectable to proximal half-section 150a by a plurality of fasteners. When joined, proximal and distal half-sections 150a, 150b define an inner handle housing 150 having an inner housing cavity (not shown) therein in which a power-pack core assembly (not shown) is situated. The power-pack core assembly is configured to control the various operations of surgical instrument 10.

Inner handle housing 150 of power pack 101 provides a housing in which the power-pack core assembly is situated. The power-pack core assembly includes a battery circuit (not shown), a controller circuit board (not shown) and a rechargeable battery (not shown) configured to supply power to any of the electrical components of handle assembly 100. The controller circuit board includes a motor controller circuit board (not shown), a main controller circuit board (not shown), and a first ribbon cable (not shown) interconnecting the motor controller circuit board and the main controller circuit board.

The power-pack core assembly further includes a motor "M" electrically connected to the controller circuit board and the battery. It is contemplated that the power-pack core assembly may include more than one motor, for example, a second motor (not shown) and a third motor (not shown). Motor "M" is disposed between the motor controller circuit board and the main controller circuit board. The power-pack core assembly has a motor shaft or drive shaft 304 (also see FIG. 5) coupled to and rotatable by motor "M."

Motor "M" is controlled by a motor controller. The motor controller is disposed on the motor controller circuit board and is, for example, A3930/31K motor drivers from Allegro Microsystems, Inc. The A3930/31K motor drivers are designed to control a 3-phase brushless DC (BLDC) motor with N-channel external power MOSFETs, such as motor "M". Each of the motor controllers is coupled to a main controller disposed on the main controller circuit board. The main controller is also coupled to memory, which is also disposed on the main controller circuit board. The main controller is, for example, an ARM Cortex M4 processor from Freescale Semiconductor, Inc, which includes 1024 kilobytes of internal flash memory. The main controller communicates with the motor controllers through an FPGA, which provides control logic signals (e.g., coast, brake, etc.). The control logic of the motor controller then outputs corresponding energization signals to motor "M" using fixed-frequency pulse width modulation (PWM).

Rotation of the motor shafts by the motors of power pack 101 function to drive shafts and/or gear components of adapter assembly 200 in order to perform the various operations of surgical instrument 10. For example, motor "M" of power-pack 101 may be configured to drive shafts and/or gear components of outer shell housing 110, which drive corresponding driven shafts and/or gear components of adapter assembly 200 in order to selectively move tool assembly 404 (FIG. 1) of SULU 400 relative to proximal body portion 402 of SULU 400, to rotate SULU 400 about a longitudinal axis "X", to move cartridge assembly 408 relative to anvil assembly 406 of SULU 400, and/or to fire staples from within cartridge assembly 408 of SULU 400.

With reference to FIGS. 1-4C, adapter assembly 200 of surgical instrument 10 is configured to transfer an axial translation of driven shaft 304 (FIG. 3), which is disposed in outer shell housing 110, to SULU 400. Adapter assembly 200 includes an outer knob housing 202 and an outer tube 206 extending from a distal end of knob housing 202. Knob housing 202 and outer tube 206 are configured and dimensioned to house the components of adapter assembly 200. Outer tube 206 is dimensioned for endoscopic insertion. In particular, outer tube 206 is passable through a typical trocar port, cannula or the like. Knob housing 202 is dimensioned to not enter the trocar port, cannula or the like. Knob housing 202 is configured and adapted to connect to connecting portion 120 of outer shell housing 110 of handle assembly 100.

With reference to FIGS. 5-10, various embodiments of a drive assembly of surgical instrument 10 are illustrated. Each drive assembly extends longitudinally through power pack 101 of handle assembly 100, through outer shell housing 110 of handle assembly 110, and through adapter assembly 200. The drive assemblies of FIGS. 5-10 are configured to transfer rotational motion originating from motor "M" of power pack 101 into axial translation of a drive member, for example, drive member 312 (FIG. 5), disposed within outer shell housing 110. This motion, in turn, is transferred to a drive member 322 (FIG. 5) disposed within adapter assembly 200, to ultimately effect surgical functions of surgical loading unit 400. As such, rotational motion originating from motor "M" of power pack 101 is converted into axial translation (i.e., movement along longitudinal axis "X") of the drive assembly at a location within outer shell housing 110. In some embodiments, rotational motion of components of the drive assembly may be converted into axial translation of components of the drive assembly at a location other than outer shell housing 110, for example, within power pack 101 or within adapter assembly 200.

Figure 5:
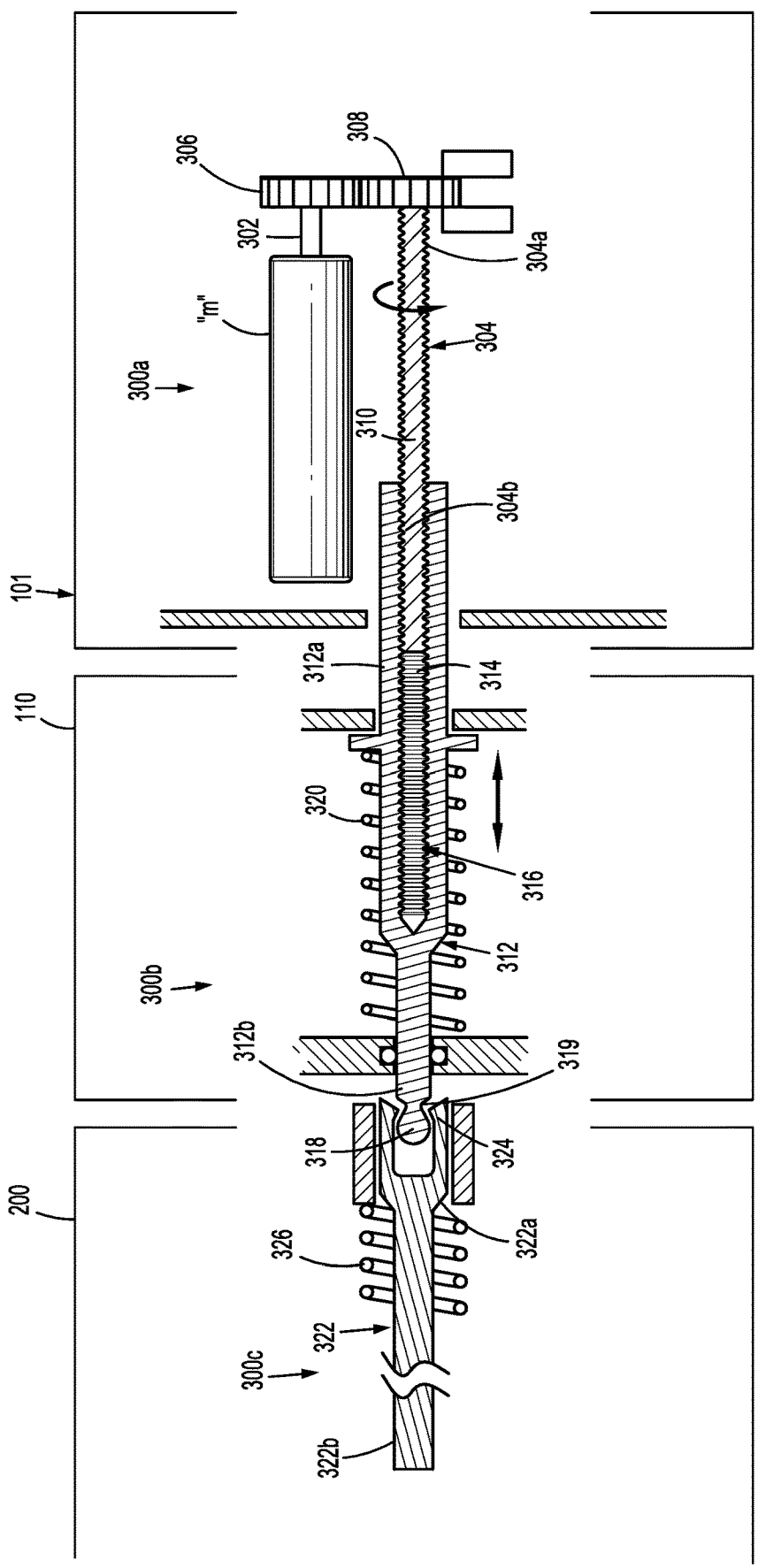
FIG. 5 is a side, cross-sectional view of one embodiment of a drive assembly that extends longitudinally through the power pack of FIG. 3, the outer shell housing of FIG. 3, and the adapter assembly of FIG. 1.

With reference to FIG. 5, one embodiment of a drive assembly 300 is shown and generally includes a first drive assembly 300a disposed within power pack 101, a second drive assembly 300b disposed within outer shell housing 110, and a third drive assembly 300c disposed within adapter assembly 200. First drive assembly 300a of power pack 101 is operably coupled to second drive assembly 300b of outer shell housing 110 upon closing outer shell housing 110 with power pack 101 disposed therein, and second drive assembly 300b of outer shell housing 110 is operably coupled to third drive assembly 300c of adapter assembly 200 upon attaching adapter assembly 200 to handle assembly 100.

First drive assembly 300a of power pack 101 includes a first drive shaft 302 coupled to and extending from motor "M" of power pack 101, and a second drive shaft or lead screw 304. First drive shaft 302 has a gear, for example, a spur gear 306, non-rotatably coupled thereto. Second drive shaft 304 has a proximal portion 304a and a distal portion 304b. Proximal portion 304a of second drive shaft 304 has a gear 308 non-rotatably coupled thereto that is in operable engagement or meshing engagement with gear 306 of first drive shaft 302 such that rotation of first drive shaft 302, caused by actuation of motor "M," drives a rotation of second drive shaft 304 within power pack 101. Distal portion 304b of second drive shaft 304 has a threaded outer surface 310 configured for a detachable threading engagement with a threaded internal surface 314 of a drive member 312 of second drive assembly 300b of outer shell housing 110.

Figure 6:
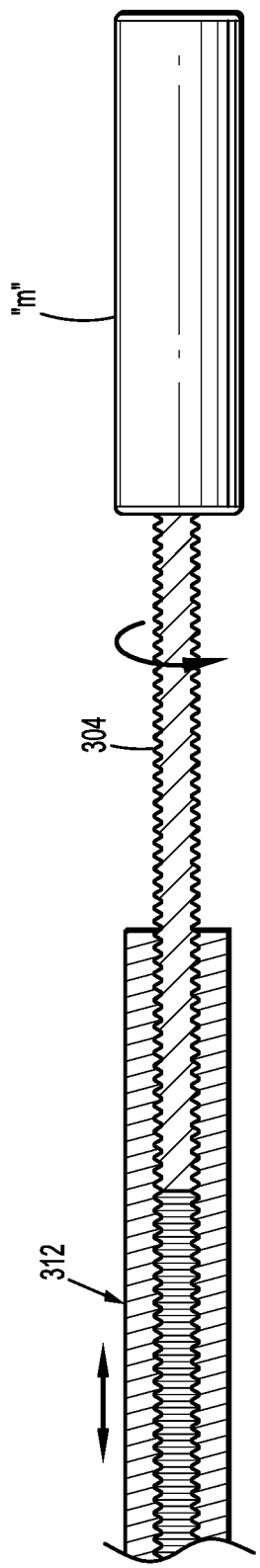
FIG. 6 is a side, cross-sectional view of another embodiment of a drive assembly that extends longitudinally through the power pack of FIG. 3, the outer shell housing of FIG. 3, and the adapter assembly of FIG. 1.

In one embodiment, as shown in FIG. 6, instead of first drive assembly 300a having two drive shafts as illustrated in FIG. 5, first drive assembly 300a of power pack 101 may have one drive shaft in the form of a lead screw 304 that extends directly and distally from motor "M."

With continued reference to FIG. 5, second drive assembly 300b is disposed within distal-half section 110b of outer shell housing 110 of handle assembly 100 and extends along longitudinal axis "X" of surgical instrument 10. Second drive assembly 300b includes a drive member, such as, for example, an elongated nut 312 that is non-rotatably supported in distal half-section 110b of outer shell housing 110. Elongated nut 312 has a proximal portion 312a and a distal portion 312b. Proximal portion 312a of second drive assembly 300b has a threaded internal surface 314 that defines a bore 316 longitudinally therethrough. Upon closing outer shell housing 110 with power pack 101 disposed therein, distal portion 304b of second drive shaft 304 of first drive assembly 300a engages threaded internal surface 314 of drive member 312 of second drive assembly 300b. To operatively couple first and second drive assemblies 300a, 300b to one another, second drive shaft 304 is rotated, which results in the threaded coupling between second drive shaft 304 of first drive assembly 300a and elongated nut 312 of second drive assembly 300b.

Distal portion 312b of elongated nut 312 of second drive assembly 300b is configured to releasably connect to third drive assembly 300c of adapter assembly 200 upon connecting knob housing 202 of adapter assembly 200 to distal half-section 110b of outer shell housing 110. In particular, distal portion 312b of elongated nut 312 may have a rounded joint or ball 318. Joint or ball 318 of elongated nut 312 may project distally outside of distal half-section 110b of outer shell housing 110. Second drive assembly 300b of outer shell housing 110 further includes a biasing member or coil spring 320 disposed about elongated nut 312. Coil spring 320 resiliently biases elongated nut 312 in a proximal direction to assist in assembly of first drive assembly 300a with second drive assembly 300b. When first and second drive assemblies 300a, 300b are operably connected to one another, a rotation of second drive shaft 304 of first drive assembly 300a drives an axial translation of elongated nut 312 of second drive assembly 300b.

With continued reference to FIG. 5, third drive assembly 300c is disposed within adapter assembly 200 and extends along longitudinal axis "X." Third drive assembly 300c includes a drive member 322 supported in knob housing 202 of adapter assembly 200 and may project proximally therefrom. Drive member 322 of third drive assembly 300c has a proximal end 322a and a distal end 322b. Proximal end 322a of drive member 322 of third drive assembly 300c may be in the form of a collet that is configured to releasably receive joint 318 of elongated nut 312 of second drive assembly 300b. Collet 322a has a pair of resilient arms 324 that snap fittingly engage cutouts 319 defined in joint 318 of elongated nut 312 of second drive assembly 300b. Distal end 322b of drive member 322 of third drive assembly 300c is configured to operatively couple to a component (not shown) of surgical loading unit 400 (FIG. 1) and to operate a function or functions of surgical loading unit 400. Third drive assembly 300c further includes a biasing member or coil spring 326 disposed about drive member 322. Coil spring 326 resiliently biases drive member 322 in a proximal direction to assist in assembly of second drive assembly 300b with third drive assembly 300c.

To assemble surgical instrument 10, proximal and distal half-sections 110a, 110b of outer shell housing 110 are pivoted away from one another to open outer shell housing 110 as described above with reference to FIGS. 4A-C. With outer shell housing 110 of handle assembly 100 in the open configuration, power pack 101, which may be in a non-sterilized state, is inserted into outer shell housing 110, which is sterile. Proximal and distal half-sections 110a, 110b of outer shell housing 110 are pivoted toward one another to close outer shell housing 110. Upon closing outer shell housing 110 with power pack 101 situated therein, first and second drive assemblies 300a, 300b engage one another.

In particular, with reference to FIG. 5, during a closure of outer shell housing 110 (See FIG. 4C), second drive shaft 304 of first drive assembly 300a of power pack 101 engages elongated nut 312 of second drive assembly 300b of outer shell housing 110 to move elongated nut 312 in a distal direction against the proximally-oriented bias imparted on elongated nut 312 by coil spring 320. In this state, first and second drive assemblies 300a, 300b are not yet operatively coupled to one another. To operatively couple first and second drive assemblies 300a, 300b, motor "M" of power pack 101 is actuated to rotate second drive shaft 304 of first drive assembly 300a. Rotation of second drive shaft 304 of first drive assembly 300a causes threaded outer surface 310 of second drive shaft 304 to catch threaded internal surface 314 of elongated nut 312 to ultimately cause second drive shaft 304 to be disposed within bore 316 of elongated nut 312.

With first drive assembly 300a of power pack 101 operatively coupled to second drive assembly 300b of outer shell housing 110, third drive assembly 300c of adapter assembly 200 may then be operatively coupled to second drive assembly 300b of outer shell housing 110. It is contemplated that adapter assembly 200 may be operatively coupled to outer shell housing 110 prior to operatively coupling power pack 101 to outer shell housing 110. To operatively couple adapter assembly 200 to outer shell housing 110, the drive coupling assembly (not shown) of knob housing 202 of adapter assembly 200 is received within connecting portion 120 (FIG. 3) of distal half-section 110b of outer shell housing 110. Upon connecting knob housing 202 of adapter assembly 200 with distal half-section 110b of outer shell housing 110, collet 322a of drive member 322 of adapter assembly 200 receives joint 318 of elongated nut 312 of outer shell housing 110 to operatively couple drive member 322 of adapter assembly 200 to elongated nut 312 of outer shell housing 110.

After surgical instrument 10 is assembled, operation of surgical instrument 10 may be performed. In particular, to effect surgical functions of surgical loading unit 400, a motor, for example, motor "M" of power pack 101 is actuated, which rotates first drive shaft 302 of power pack 100, and in turn, rotates second drive shaft 304 of power pack 101, via the interactions between gears 306, 308 of first and second drive shafts 302, 304, respectively. The rotation of second drive shaft 304 drives a proximal or distal longitudinal movement of elongated nut 312 of outer shell housing 110 due to second drive shaft 304 of power pack 101 being threadingly engaged to elongated nut 312 of outer shell housing 110. Proximal or distal longitudinal movement of elongated nut 312 results in a corresponding motion of drive member 322 of adapter assembly 200 as a result of elongated nut 312 of outer shell housing 110 being attached to drive member 322 of adapter assembly 200. Since distal end 322b of drive member 322 of adapter assembly 200 is operatively connected to a working component(s) (not shown) of surgical loading unit 400, the axial movement of drive member 322 of adapter assembly 200 effects various functions of surgical loading unit 400, for example, opening or closing of its jaw members 406, 408, a stapling function, and/or a cutting function.

To disassemble surgical instrument 10, knob housing 202 of adapter assembly 200 may be manually detached from handle assembly 100, thereby causing joint 318 of elongated nut 312 of outer shell housing 110 to disengage collet 322a of drive member 322 of adapter assembly 200. Prior to removing power pack 101 from outer shell housing 110, first drive assembly 300a of power pack 101 is disengaged from second drive assembly 300b. To disengage first and second drive assemblies 300a, 300b from one another, motor "M" of power pack 101 is actuated to rotate first drive shaft 302, and in turn, second drive shaft 304. Rotation of second drive shaft 304 of first drive assembly 300a causes second drive shaft 304 of first drive assembly 300a to back out of bore 316 of elongated nut 312 by pushing elongated nut 312 in a distal direction. Second drive shaft 304 is rotated until its threaded outer surface 310 is out of threading engagement with threaded internal surface 314 of elongated nut 312. After disengaging second drive shaft 304 of power pack 101 from elongated nut 312 of outer shell housing 110, snap closure feature 118 of outer shell housing 110 is unsnapped and outer shell housing 110 is opened. With outer shell housing 110 in the opened configuration, as shown in FIG. 4B, power pack 101 can be removed from outer shell housing 110. Outer shell housing 110 may then be re-sterilized or re-cleaned for re-use.

Figure 7:
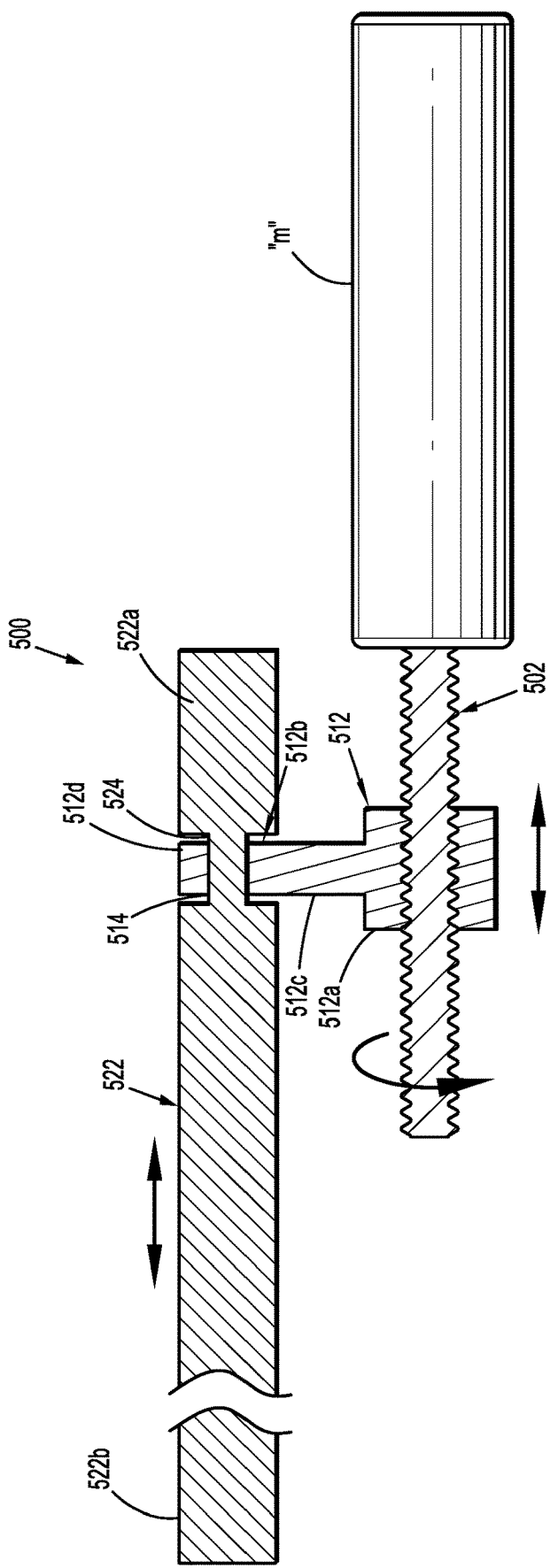
FIG. 7 is a side, cross-sectional view of yet another embodiment of a drive assembly that extends longitudinally through the power pack of FIG. 3, the outer shell housing of FIG. 3, and the adapter assembly of FIG. 1.

With reference to FIG. 7, another embodiment of a drive assembly is illustrated, which is similar to drive assembly 300 described above with reference to FIG. 5, thus, to prevent unnecessary repetition only the differences between the embodiments are described. Drive assembly 500 generally includes a drive shaft or lead screw 502 disposed within power pack 101, a drive member 512 disposed within outer shell housing 110, and a drive member 522 disposed within adapter assembly 200. Lead screw 502 of power pack 101 is operably coupled to drive member 512 of outer shell housing 110 upon closing outer shell housing 110 with power pack 101 disposed therein, and drive member 512 of outer shell housing 110 is operably coupled to drive member 522 of adapter assembly 200 upon attaching adapter assembly 200 to handle assembly 100.

Lead screw 502 of drive assembly 500 is disposed within power pack 101 and is coupled to and extends from motor "M" of power pack 101. Drive member 512 of outer shell housing 110 is in the form of a coupling member that is configured to convert a rotation of lead screw 502 of power pack 101 into a translation of drive assembly 500 within outer shell housing 110. Coupling member 512 is restrained within power pack 101 so as to prevent coupling member 512 from rotating therein. Coupling member 512 of drive assembly 500 is disposed within outer shell housing 110 and has a nut 512a, and a post 512b extending from nut 512a. Nut 512a of coupling member 512 is configured to be threadingly engaged to lead screw 502 of power pack 101 such that rotation of lead screw 502 of power pack 101, caused by actuation of motor "M" of power pack 101, causes coupling member 512 of outer shell housing 110 to translate along lead screw 502. Post 512b of coupling member 512 has a first end 512c and a second end 512d and extends along an axis that is perpendicular to longitudinal axis "X" of surgical instrument 10. First end 512c of post 512b is monolithically formed with nut 512a, but it is contemplated that first end 512c of post 512b may be attached to nut 512a via any suitable engagement. Second end 512b of post 512b has a mating part 514 configured for detachable mating with a corresponding mating part 524 of drive member 522 of adapter assembly 200. Mating part 514 is a step or squared cutout defined in second end 512d of post 512b. In some embodiments, mating part 514 of coupling member 512 may be any suitable male or female mating part.

Drive member 522 of drive assembly 500 is disposed within adapter assembly 200 and extends along longitudinal axis "X" of surgical instrument 10. Drive member 522 is an elongated shaft having a proximal end 522a and a distal end 522b. Proximal end 522a of drive member 522 has a mating part 524, similar to mating part 514 of coupling member 512 outer shell housing 110. Mating part 524 of drive member 522 of adapter assembly 200 is configured for detachable mating with mating part 514 of coupling member 512 of outer shell housing 110. Distal end 522b of drive member 522 of adapter assembly 200 is configured to operatively couple to a component (not shown) of surgical loading unit 400 to operate a function or functions of surgical loading unit 400.

To assemble surgical instrument 10, proximal and distal half-sections 110a, 110b of outer shell housing 110 are pivoted away from one another to open outer shell housing 110. With outer shell housing 110 of handle assembly 100 in the open configuration, as shown in FIG. 4B, power pack 101, which may be in a non-sterilized state, is inserted into outer shell housing 110, which is sterile. Proximal and distal half-sections 110a, 110b of outer shell housing 110 are pivoted toward one another to close outer shell housing 110. Upon closing outer shell housing 110 with power pack 101 situated therein, drive assembly 500 is assembled.

In particular, during a closure of outer shell housing 110, lead screw 502 of power pack 101 engages nut 512a of coupling member 512 of outer shell housing 110 to move coupling member 512 in a distal direction against a proximally oriented bias imparted on coupling member 512 by a coil spring (not shown). With drive assembly 500 in this state, lead screw 502 of power pack 101 and coupling member 512 of outer shell housing 110 are not yet operatively coupled to one another. To operatively couple lead screw 502 to coupling member 512, motor "M" of power pack 101 is actuated to rotate lead screw 502 of power pack 101. Rotation of lead screw 502 of power pack 101 causes a threaded outer surface of lead screw 502 to catch a threaded internal surface (not shown) of nut 512a of coupling member 512 to ultimately cause lead screw 502 to be disposed within nut 512a of coupling member 512.

With lead screw 502 of power pack 101 operatively coupled to coupling member 512 of outer shell housing 110, adapter assembly 200 may then be operatively coupled to outer shell housing 110. It is contemplated that adapter assembly 200 may be operatively coupled to outer shell housing 110 prior to operatively coupling power pack 101 to outer shell housing 110. To operatively couple adapter assembly 200 to outer shell housing 110, the drive coupling assembly (not shown) of knob housing 202 of adapter assembly 200 is received within connecting portion 120 (FIG. 3) of distal half-section 110b of outer shell housing 110. Upon connecting knob housing 202 of adapter assembly 200 with distal half-section 110b of outer shell housing 110, mating part 524 of drive member 522 of adapter assembly 200 interlocks with mating part 514 of coupling member 512 of outer shell housing 110 to operatively couple drive member 522 of adapter assembly 200 to coupling member 512 of outer shell housing 110.

After drive assembly 500 of surgical instrument 10 is assembled, operation of surgical instrument 10 may be performed. In particular, to effect surgical functions of surgical loading unit 400, motor "M" of power pack 101 is actuated, which rotates lead screw 502 of power pack 101. Rotation of lead screw 502 of power pack 101 drives a proximal or distal longitudinal movement of coupling member 512 of outer shell housing 110 therealong. Proximal or distal longitudinal movement of coupling member 512 of outer shell housing 110 results in a corresponding motion of drive member 522 of adapter assembly 200 as a result of coupling member 512 of outer shell housing 110 being attached to drive member 522 of adapter assembly 200. Since distal end 522b of drive member 522 of adapter assembly 200 is operatively connected to working component(s) (not shown) of surgical loading unit 400, the axial movement of drive member 522 of adapter assembly 200 effects various functions of surgical loading unit 400, for example, opening or closing of its jaw members 406, 408, a stapling function, and/or a cutting function.

To disassemble surgical instrument 10, knob housing 202 of adapter assembly 200 may be manually detached from handle assembly 100, thereby causing mating part 524 of drive member 522 of adapter assembly 200 to disengage mating part 514 of coupling member 512 of outer shell housing 110. Prior to removing power pack 101 from outer shell housing 110, lead screw 502 of power pack 101 is disengaged from coupling member 512 of outer shell housing 110. To disengage lead screw 502 from coupling member 512, motor "M" of power pack 101 is actuated to rotate lead screw 502. Rotation of lead screw 502 of power pack 101 causes lead screw 502 of power pack 101 to back out of nut 512a of coupling member 512 while pushing coupling member 512 in a distal direction. Rotation of lead screw 502 of power pack 101 is continued until its threaded outer surface is out of threading engagement with the threaded internal surface of nut 512a of coupling member 512 of outer shell housing 110. After disengaging lead screw 502 of power pack 101 from coupling member 512 of outer shell housing 110, snap closure feature 118 of outer shell housing 110 is unsnapped and outer shell housing 110 is opened. With outer shell housing 110 in the open configuration, power pack 101 can be removed from outer shell housing 110.

With reference to FIGS. 8A and 8B, another embodiment of a drive assembly 600 is illustrated, similar to drive assemblies 300, 500 described above with reference to FIGS. 5-7. Drive assembly 600 generally includes a drive shaft assembly 602 disposed within power pack 101, a drive member 612 disposed within outer shell housing 110, and a drive member 622 disposed within adapter assembly 200. Drive shaft assembly 602 of power pack 101 is operably coupled to drive member 612 of outer shell housing 110 upon closing outer shell housing 110 with power pack 101 disposed therein, and drive member 612 of outer shell housing is operably coupled to the drive member (not shown) of adapter assembly 200 upon attaching adapter assembly 200 to handle assembly 100.

Drive shaft assembly 602 of drive assembly 600 is disposed within power pack 101 and includes a drive shaft 604 coupled to and extending from motor "M" of power pack 101, a first gear 606, and a second gear or coupling gear 608. First gear 606 is non-rotatably coupled to drive shaft 604 and defines a rotation axis that is parallel to longitudinal axis "X" of surgical instrument 10. First gear 606 is in the form of a bevel gear, but in some embodiments, first gear 606 may be any suitable gear. Second gear or coupling gear 608 is in operable engagement or meshing engagement with first gear 606. Coupling gear 608 defines a rotation axis that is perpendicular to the rotation axis of first gear 606. Coupling gear 608 is a compound bevel-spur gear. Specifically, coupling gear 608 includes a bevel gear 608a and a spur gear 608b extending from bevel gear 608a. Bevel gear 608a of coupling gear 608 is in operable engagement with first gear 606 of drive shaft 604. Spur gear 608b of coupling gear 608 is configured to be in operable engagement with drive member 612 of outer shell housing 110 upon closing outer shell housing 110 around power pack 101.

Drive member 612 of outer shell housing 110 is in the form of a longitudinal rack that is configured to convert a rotation of coupling gear 608 of power pack 101 into a translation of drive assembly 600 within outer shell housing 110. Rack 612 of outer shell housing 110 has a proximal portion 612a and a distal portion (not explicitly shown) and extends along longitudinal axis "X" of surgical instrument 10. Proximal portion 612a has a plurality of teeth 614 configured to operably engage or meshingly engage spur gear 608b of second gear 608 such that rotation of coupling gear 608 of power pack 101, caused by actuation of motor "M" of power pack 101, causes rack 612 of outer shell housing 110 to axially translate. The distal end of rack 612 of outer shell housing 110 is configured for detachable mating engagement with a mating part of the drive member (not shown) of adapter assembly 200. It is contemplated that the distal end of rack 612 and a proximal end of the drive member of adapter assembly 200 releasably engage one another in a similar manner as that described with reference to second and third drive assemblies 300b, 300c of FIG. 5. The distal end of the drive member of adapter assembly 200 is configured to operatively couple to component(s)(not shown) of surgical loading unit 400 to operate a function or functions of surgical loading unit 400.

To assemble surgical instrument 10, proximal and distal half-sections 110a, 110b of outer shell housing 110 are pivoted away from one another to open outer shell housing 110. With outer shell housing 110 of handle assembly 100 in the open configuration, power pack 101, which may be in a non-sterilized state, is inserted into a sterilized outer shell housing 110. Proximal and distal half-sections 110a, 110b of outer shell housing 110 are pivoted toward one another to close outer shell housing 110. Upon closing outer shell housing 110 with power pack 101 situated therein, drive assembly 600 is assembled.

In particular, during a closure of outer shell housing 110, spur gear 608b of coupling gear 608 of power pack 101 engages teeth 614 of rack 612 of outer shell housing 110. Adapter assembly 200 may then be operatively coupled to outer shell housing 110 in a similar manner described above with reference to FIGS. 5-7. It is contemplated that adapter assembly 200 may be operatively coupled to outer shell housing 110 prior to operatively coupling power pack 101 to outer shell housing 110.

After drive assembly 600 of surgical instrument 10 is assembled, operation of surgical instrument 10 may be performed. In particular, to effect surgical functions of surgical loading unit 400, motor "M" of power pack 101 is actuated, which rotates first gear 606 of power pack 101. Rotation of first gear 606 drives a rotation of coupling gear 608, which in turn drives a proximal or distal longitudinal movement of rack 612 of outer shell housing 110. Proximal or distal longitudinal movement of rack 612 of outer shell housing 110 results in a corresponding motion of the drive member of adapter assembly 200 as a result of rack 612 of outer shell housing 110 being attached to the drive member of adapter assembly 200. Since the distal end of the drive member of adapter assembly 200 is operatively connected to working component(s) (not shown) of surgical loading unit 400, the axial movement of the drive member of adapter assembly 200 effects various functions of surgical loading unit 400, for example, opening or closing of its jaw members 406, 408, a stapling function, and/or a cutting function.

To disassemble surgical instrument 10, knob housing 202 of adapter assembly 200 may be manually detached from handle assembly 100, in a similar manner described above with respect to FIGS. 5-7. Snap closure feature 118 of outer shell housing 110 is unsnapped and outer shell housing 110 is opened, as shown in FIG. 4B. With outer shell housing 110 in the open configuration, power pack 101 can be removed from outer shell housing 110.

Figure 9:
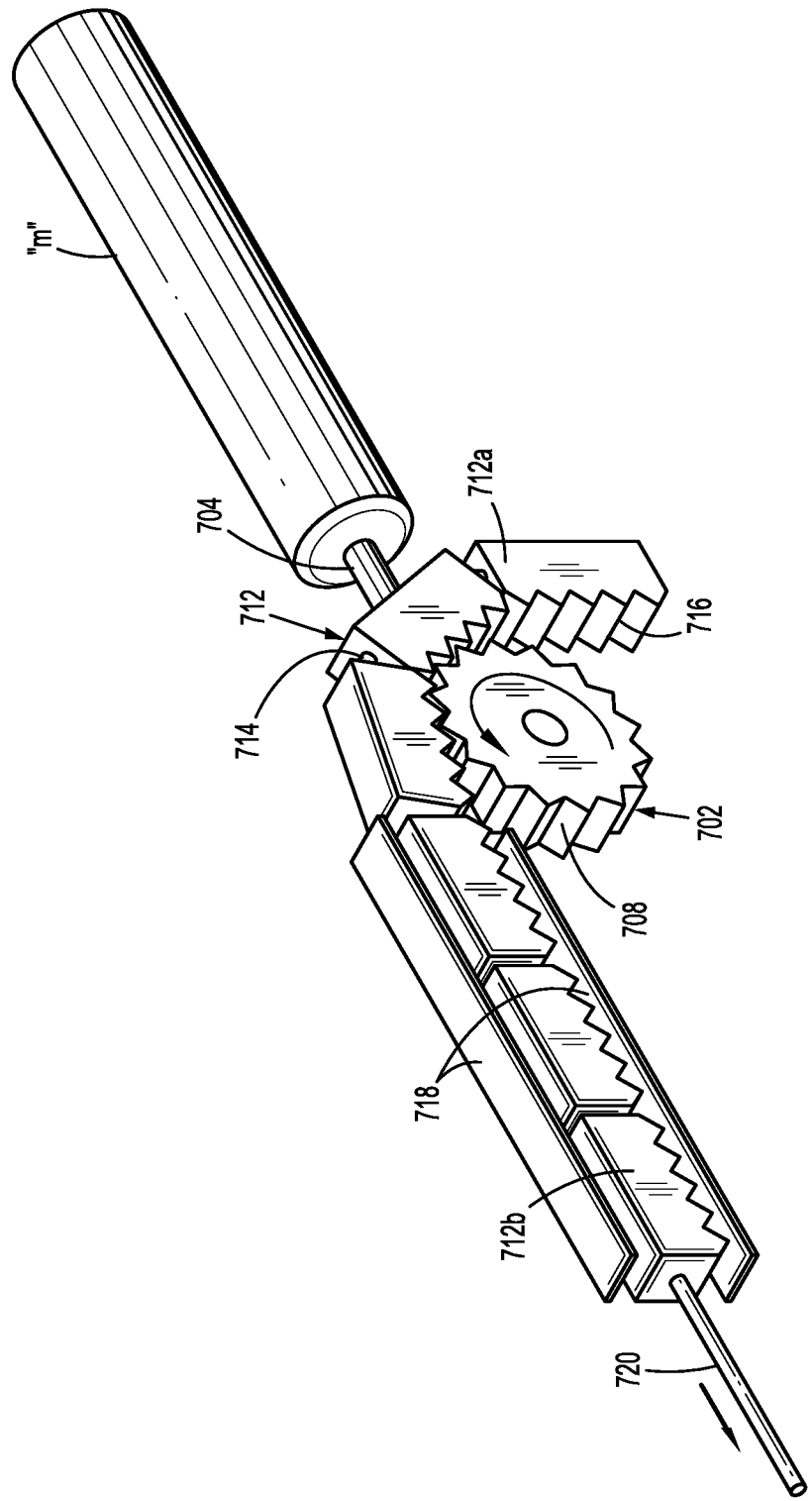
FIG. 9 is a perspective view of yet another embodiment of a drive assembly that extends longitudinally through the power pack of FIG. 3, the outer shell housing of FIG. 3, and the adapter assembly of FIG. 1.

With reference to FIG. 9, another embodiment of a drive assembly 700 is illustrated, similar to drive assemblies 300, 500, 600 described above with reference to FIGS. 5-8B. Drive assembly 700 generally includes a drive shaft assembly 702 disposed within power pack 101, a drive member 712 disposed within outer shell housing 110, and a drive member (not shown) disposed within adapter assembly 200. Drive shaft assembly 702 of power pack 101 is operably coupled to drive member 712 of outer shell housing 110 upon closing outer shell housing 110 with power pack 101 disposed therein, and drive member 712 of outer shell housing 110 is operably coupled to the drive member of adapter assembly 200 upon attaching adapter assembly 200 to handle assembly 100.

Drive shaft assembly 702 of drive assembly 700 is disposed within power pack 101 and includes a drive shaft 704 coupled to and extending from motor "M" of power pack 101, a first gear (not explicitly shown), and a second gear or coupling gear 708. Drive shaft assembly 702 of power pack 101 is similar to drive shaft assembly 602 described above with reference to FIGS. 8A and 8B, and will therefore not be described in detail herein.

Drive member 712 of outer shell housing is in the form of a plurality of racks that are configured to convert a rotation of coupling gear 708 of power pack 101 into a translation of drive assembly 700 within outer shell housing 110. Racks 712 of outer shell housing 110 are coupled to one another to form a train of racks. Each rack 712 may be coupled to an adjacent rack 712 by a ball and socket connection 714, a relatively rigid tether, or any other suitable connection that permits racks 712 to pivot relative to one another, but resists pivoting of racks 712 relative to one another unless a threshold force is applied. As such, racks 712 will maintain a generally linear configuration if no force is acting on racks 712. Racks 712 each have a concave surface having teeth 716 projecting therefrom. The toothed surface 716 of each rack 712 is concave to cup coupling gear 708 of power pack 101 upon outer shell housing 110 closing around power pack 101. Racks 712 are disposed between two plates or tracks 718 that are fixed within distal half-section 110b of outer shell housing 110. Plates 718 prevent racks 712 from buckling, thereby guiding racks 712 along longitudinal axis "X."

Drive assembly 700 further includes a firing rod or shaft 720 extending distally from a distal-most rack 712b. A distal end of firing rod 720 of outer shell housing 110 is configured for detachable mating engagement with a mating part (not shown) of the drive member (not shown) of adapter assembly 200. It is contemplated that the distal end of firing rod 720 of outer shell housing 110 and a proximal end of the drive member of adapter assembly 200 releasably engage one another in a similar manner as that described with reference to second and third drive assemblies 300b, 300c of FIG. 5. The distal end of the drive member of adapter assembly 200 is configured to operatively couple to a component(s)(not shown) of surgical loading unit 400 to operate a function or functions of surgical loading unit 400.

To assemble surgical instrument 10, proximal and distal half-sections 110a, 110b of outer shell housing 110 are pivoted away from one another to open outer shell housing 110. With outer shell housing 110 of handle assembly 100 in the open configuration, as shown in FIG. 4B, power pack 101, which may be in a non-sterilized state, is inserted into a sterilized outer shell housing 110. Proximal and distal half-sections 110a, 110b of outer shell housing 110 are pivoted toward one another to close outer shell housing 110. Upon closing outer shell housing 110 with power pack 101 situated therein, drive assembly 700 is assembled.

In particular, during a closure of outer shell housing 110, the spur gear 708 of coupling gear of power pack 101 engages teeth 716 of a proximal-most rack 712a of outer shell housing 110. Adapter assembly 200 may then be operatively coupled to outer shell housing 110 in a similar manner described above with reference to FIGS. 5-7. It is contemplated that adapter assembly 200 may be operatively coupled to outer shell housing 110 prior to operatively coupling power pack 101 to outer shell housing 110.

After drive assembly 700 of surgical instrument 10 is assembled, operation of surgical instrument 10 may be performed. In particular, to effect surgical functions of surgical loading unit 400, motor "M" of power pack 101 is actuated, which rotates first gear (not explicitly shown) of power pack 101. Rotation of the first gear drives a rotation of second gear 708, which in turn drives a proximal or distal longitudinal movement of racks 712 of outer shell housing 110 through tracks 718 of outer shell housing 110. Proximal or distal longitudinal movement of racks 712 of outer shell housing 110 results in a corresponding motion of firing rod 720 of outer shell housing 110 and the drive member (not shown) of adapter assembly 200 as a result of firing rod 720 of outer shell housing 110 being attached to the drive member of adapter assembly 200. Since the distal end of the drive member of adapter assembly 200 is operatively connected to a working component(s)(not shown) of surgical loading unit 400, the axial movement of the drive member of adapter assembly 200 effects various functions of surgical loading unit 400, for example, opening or closing of its jaw members 406, 408, a stapling function, and/or a cutting function.

To disassemble surgical instrument 10, knob housing 202 of adapter assembly 200 may be manually detached from handle assembly 100, in a similar manner described above with respect to FIGS. 5-7. Snap closure feature 118 of outer shell housing 110 is unsnapped and motor "M" of power pack 101 is actuated until each of racks 712 are out of engagement with second gear 708 of power pack 101 and proximal-most rack 712a is disposed distally of second gear 708 of power pack 101. Outer shell housing 110 may then be opened. With outer shell housing 110 in the open configuration, as shown in FIG. 4B, power pack 101 can be removed from outer shell housing 110.

Figure 10:
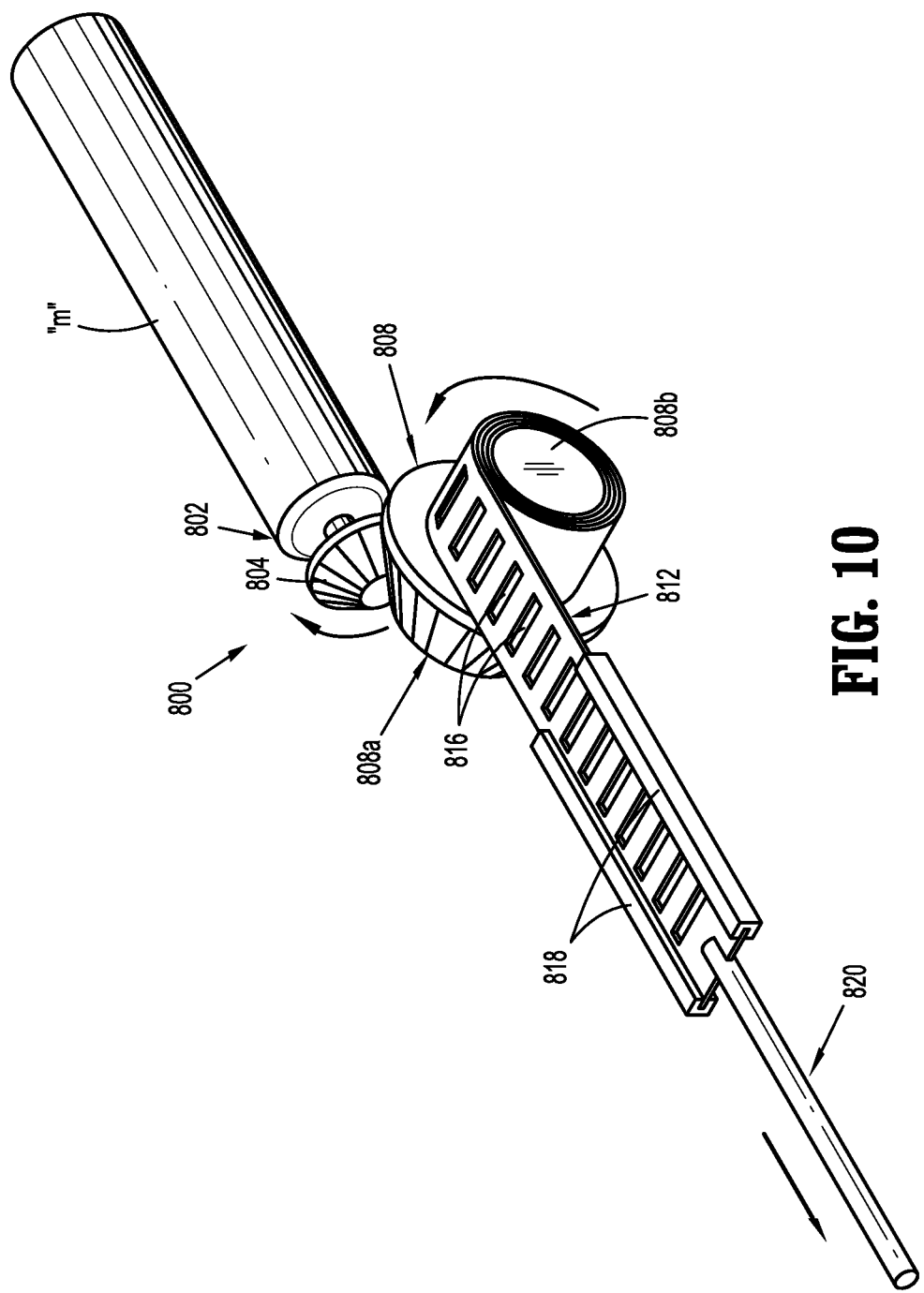
FIG. 10 is a perspective view of yet another embodiment of a drive assembly that extends longitudinally through the power pack of FIG. 3, the outer shell housing of FIG. 3, and the adapter assembly of FIG. 1.

With reference to FIG. 10, another embodiment of a drive assembly 800 is illustrated, similar to drive assembly 700 described above with reference to FIG. 9. Drive assembly 800 generally includes a drive shaft assembly 802 disposed within power pack 101, a drive member 812 disposed within outer shell housing 110, and a drive member (not shown) disposed within adapter assembly 200. Drive shaft assembly 802 of power pack 101 is operably coupled to drive member 812 of outer shell housing 110 upon closing outer shell housing 110 with power pack 101 disposed therein, and drive member 812 of outer shell housing 110 is operably coupled to the drive member of adapter assembly 200 upon attaching adapter assembly 200 to handle assembly 100, as will be described in detail below.

Drive shaft assembly 802 of drive assembly 800 is disposed within power pack 101 and includes a drive shaft (not explicitly shown) coupled to and extending from motor "M" of power pack 101, a first gear 804, and a second gear or coupling gear 808. Drive shaft assembly 802 of power pack 101 is similar to drive shaft assembly 602 described above with reference to FIGS. 8A and 8B, and will therefore not be described in further detail herein.

Drive member 812 of outer shell housing 110 is in the form of an elongated ribbon that is configured to convert a rotation of second gear 808 of power pack 101 into a translation of drive assembly 800 within outer shell housing 110. Ribbon 812 of outer shell housing 110 resists bending or folding unless a threshold force is applied. As such, ribbon 812 will maintain a generally linear configuration if no force is acting thereon. Ribbon 812 defines a plurality of slits 816 therein configured for receipt of teeth of spur gear 808b of second gear 808 of power pack 101. Ribbon 812 is disposed between two plates or tracks 818 that are fixed within distal half-section 110b of outer shell housing 110. Tracks 818 prevent ribbon 812 from buckling, thereby guiding ribbon 812 along longitudinal axis "X."

A firing rod or shaft 820 extends distally from a distal end of ribbon 812. A distal end of firing rod 820 of outer shell housing 110 is configured for detachable mating engagement with a mating part (not shown) of the drive member (not shown) of adapter assembly 200. It is contemplated that the distal end of firing rod 820 and a proximal end of the drive member of adapter assembly 200 releasably engage one another in a similar manner as that described above with reference to second and third drive assemblies 300b, 300c of FIG. 5. The distal end of the drive member of adapter assembly 200 is configured to operatively couple to a component(s)(not shown) of surgical loading unit 400 to operate a function or functions of surgical loading unit 400.

To assemble surgical instrument 10, proximal and distal half-sections 110a, 110b of outer shell housing 110 are pivoted away from one another to open outer shell housing 110, as shown in FIG. 4B. With outer shell housing 110 of handle assembly 100 in the open configuration, power pack 101, which may be in a non-sterilized state, is inserted into a sterilized outer shell housing 110. Proximal and distal half-sections 110a, 110b of outer shell housing 110 are pivoted toward one another to close outer shell housing 110. Upon closing outer shell housing 110 with power pack 101 situated therein, drive assembly 800 is assembled.

In particular, during a closure of outer shell housing 110, spur gear 808b of second gear 808 of power pack 101 are received within slits 816 defined in ribbon 812 of outer shell housing 110. Adapter assembly 200 may then be operatively coupled to outer shell housing 110 in a similar manner described above with reference to FIGS. 5-7. It is contemplated that adapter assembly 200 may be operatively coupled to outer shell housing 110 prior to operatively coupling power pack 101 to outer shell housing 110.

After drive assembly 800 of surgical instrument 10 is assembled, operation of surgical instrument 10 may be performed. In particular, to effect surgical functions of surgical loading unit 400, motor "M" of power pack 101 is actuated, which rotates first gear 804 of power pack 101. Rotation of first gear 804 drives a rotation of second gear 808, which in turn causes ribbon 812 to wrap thereabout and drives a proximal or distal longitudinal movement of ribbon 812 of outer shell housing 110 through tracks 818 of outer shell housing 110. Proximal or distal longitudinal movement of ribbon 812 of outer shell housing 110 results in a corresponding motion of firing rod 820 of outer shell housing 110 and the drive member of adapter assembly 200 as a result of firing rod 820 of outer shell housing 110 being attached to the drive member of adapter assembly 200. Since the distal end of the drive member of adapter assembly 200 is operatively connected to a working component(s)(not shown) of surgical loading unit 400, the axial movement of the drive member of adapter assembly 200 effects various functions of surgical loading unit 400, for example, opening or closing of its jaw members 406, 408, a stapling function, and/or a cutting function.

To disassemble surgical instrument 10, knob housing 202 of adapter assembly 200 may be manually detached from handle assembly 100, in a similar manner described above with respect to FIGS. 5-7. Snap closure feature 118 of outer shell housing 110 is unsnapped and motor "M" of power pack 101 is actuated until ribbon 812 unravels from around second gear 808 of power pack 101 and teeth of second gear 808 of power pack 101 are removed from slits 816 of ribbon 812. Outer shell housing 110 may then be opened. With outer shell housing 110 in the open configuration, power pack 101 can be removed from outer shell housing 110.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A surgical instrument, comprising:
   a power pack including:
      an inner handle housing;
      a motor disposed in the inner handle housing; and
      a drive shaft partially disposed in the inner handle housing and coupled to and rotatable by the motor;
   an outer shell housing configured to encase the power pack therein, the outer shell housing including a first drive member having a distal end disposed outside of and distal of the inner handle housing of the power pack, the first drive member being supported in a distal portion of the outer shell housing, the first drive member being configured to selectively couple to the drive shaft; and
   an adapter assembly having a proximal end configured to couple to a distal end of the outer shell housing, and a distal end configured to couple to a loading unit, the adapter assembly having a second drive member supported in the proximal end, the second drive member being configured to selectively couple to the distal end of the first drive member such that rotation of the drive shaft actuates the second drive member through the first drive member, wherein the first drive member is non-rotatably supported by the distal portion of the outer shell housing such that the first drive member is prevented from rotating relative to the outer shell housing about a longitudinal axis defined by the first drive member.

2. The surgical instrument according to claim 1, wherein the outer shell housing is transitionable between an open configuration, in which the power pack is at least one of insertable or removable from the outer shell housing, and a closed configuration, in which the power pack is enclosed within the outer shell housing.

3. The surgical instrument according to claim 2, wherein the outer shell housing has a proximal portion pivotably coupled to the distal portion of the outer shell housing such that in the open configuration, a portion of the proximal portion of the outer shell housing is spaced from a corresponding portion of the distal portion of the outer shell housing and in the closed configuration, the portion of the proximal portion of the outer shell housing is connected to the corresponding portion of the distal portion of the outer shell housing.

4. The surgical instrument according to claim 2, wherein in the closed configuration, the drive shaft is operably connected to the first drive member and in the open configuration, the drive shaft is disconnected from the first drive member.

5. The surgical instrument according to claim 1, wherein rotation of the drive shaft axially moves the first drive member when the first drive member is operably connected to the drive shaft of the power pack.

6. The surgical instrument according to claim 1, wherein the drive shaft is a lead screw.

7. The surgical instrument according to claim 6, wherein the first drive member of the outer shell housing is an elongated nut threadingly engaged to the lead screw such that rotation of the lead screw axially moves the elongated nut relative to the lead screw.

* * * * *